(12) United States Patent
Crivelli

(10) Patent No.: US 8,578,795 B2
(45) Date of Patent: Nov. 12, 2013

(54) MONITORING AND RECORDING IMPLANTABLE SILICON ACTIVE PRESSURE TRANSDUCER

(75) Inventor: Rocco Crivelli, Neuchâtel (CH)

(73) Assignee: DePuy Synthes Products, LLC, Raynham, MA (US)

(*) Notice: Subject to any disclaimer, the term of this patent is extended or adjusted under 35 U.S.C. 154(b) by 335 days.

(21) Appl. No.: 13/077,091

(22) Filed: Mar. 31, 2011

(65) Prior Publication Data

US 2012/0247227 A1    Oct. 4, 2012

(51) Int. Cl.
| | |
|---|---|
| G01L 1/00 | (2006.01) |
| A61B 5/04 | (2006.01) |
| A61B 5/00 | (2006.01) |
| A61B 5/02 | (2006.01) |

(52) U.S. Cl.
USPC ....... 73/862.381; 600/398; 600/561; 600/486

(58) Field of Classification Search
USPC .................. 73/862.381; 600/398, 561, 486
See application file for complete search history.

(56) References Cited

U.S. PATENT DOCUMENTS

| | | | |
|---|---|---|---|
| 4,003,141 A | 1/1977 | Le Roy | |
| 4,519,401 A | 5/1985 | Ko et al. | |
| 4,875,134 A | 10/1989 | Kuisma | |
| 5,291,899 A | 3/1994 | Watanabe et al. | |
| 5,833,603 A | 11/1998 | Kovacs et al. | |
| 6,234,973 B1 | 5/2001 | Meador et al. | |
| 6,287,256 B1 | 9/2001 | Park et al. | |
| 6,450,038 B1 | 9/2002 | Iseni et al. | |
| 6,516,670 B2 | 2/2003 | Hegner et al. | |
| 6,543,291 B1 | 4/2003 | Kurtz et al. | |
| 6,731,976 B2 | 5/2004 | Penn et al. | |
| 7,017,419 B2 | 3/2006 | Pedersen et al. | |
| 7,024,936 B2 | 4/2006 | Pedersen et al. | |
| 7,188,530 B2 | 3/2007 | Pedersen et al. | |
| 7,471,986 B2 | 12/2008 | Hatlestad | |
| 2005/0187594 A1 | 8/2005 | Hatlestad et al. | |
| 2006/0241354 A1 | 10/2006 | Allen | |
| 2006/0283007 A1 | 12/2006 | Cros et al. | |
| 2006/0287602 A1* | 12/2006 | O'Brien et al. | 600/486 |
| 2008/0079565 A1 | 4/2008 | Koyama | |

FOREIGN PATENT DOCUMENTS

| | | | |
|---|---|---|---|
| EP | 1184351 | | 3/2002 |
| EP | 1184351 | * | 4/2004 |

* cited by examiner

Primary Examiner — Lisa Caputo
Assistant Examiner — Brandi N Hopkins
(74) Attorney, Agent, or Firm — Cheryl F. Cohen, LLC

(57) ABSTRACT

An implantable active pressure transducer including a pressure sensing element and associated sensor circuitry together enclosed within an innermost glass packaging. The pressure sensing element is anodically bonded to the innermost packaging substantially aligned with an opening defined therein. An outermost biocompatible metal packaging forms a cavity divided into first and second chambers by an intermediate partition. The innermost packaging is disposed within the first chamber without physically directly contacting or being fixed to the outermost packaging. A barrier plate is hermetically sealed to the intermediate partition to hermetically isolate the battery and communication circuitry from a pressure transmitting fluid. Inductive coupling is used to communicate data detected by the pressure sensing element internally within the implant.

26 Claims, 3 Drawing Sheets

MONITORING AND RECORDING IMPLANTABLE SILICON ACTIVE PRESSURE TRANSDUCER

BACKGROUND OF THE INVENTION

1. Field of the Invention

The present invention relates to a silicon micro pressure sensor or transducer. More particularly, the invention relates to a monitoring and recording silicon active pressure sensor or transducer suitable for long term implantation in the body.

2. Description of Related Art

In order to monitor pressure within certain environments a pressure transducer or sensor is encapsulated in a hermetically sealed packaging or enclosure to protect its electronic circuitry against malfunction. EP Patent No. 1 184 351 discloses a method for brazing two glass components together to form a leak tight container for encapsulating electronic components such as a pressure transducer implanted in a human body. Many medical applications require implantable measurement devices, for example, implantable pressure transducers or sensors. Once implanted, the passive pressure transducer may be inductively coupled to a reading unit which energizes the transducer and allows the transmission between the transducer and the reading unit of data corresponding to the measured pressure.

One disadvantage associated with a passive pressure sensor activated by external RF energy only during communications with an external device is that the monitoring and recording of pressure data is dependent on communication with the external device and hence not continuous. An active pressure sensor including an internal battery is therefore desirable so that the pressure data may be monitored and recorded continuously or at least independent of communication with an external device. However, such an active implantable pressure sensor raises several design challenges. A hermetically sealed glass encapsulation of an active implantable pressure sensor is impractical due to the relatively large size requirements in order to accommodate the internal battery that would make the glass too fragile.

Another known approach disclosed in U.S. Pat. No. 6,543,291 is to encapsulate a pressure sensor in a hermetically sealed metallic enclosure resistant to certain chemical environments. Pressure outside the sealed enclosure is transmitted across its boundary by compression of a pressure transmitting medium, typically oil or mercury, that when displaced mechanically deflects a relatively thin membrane welded onto the metallic enclosure. Outside pressure deflects the metallic membrane displacing the medium within the metallic enclosure and a deflectable membrane associated with the pressure sensor element. An electrical signal produced by the electronic circuitry of the pressure sensor element is then converted to a pressure data signal by signal processing circuitry. The use of a fluid as a pressure transmitting medium may undesirably damp the measured pressure signal due to the difficulty in zeroing the compliance of the transmitting medium during manufacture of the sensor. For instance, during manufacture the welding of the metallic membrane to a titanium enclosure may cause the formation of unwanted air bubbles in the pressure transmitting medium that could damp the measured pressure signal. U.S. Pat. No. 6,450,038 discloses a mechanical transmitting mechanism rather than the fluid pressure transmitting medium. A silicon deflectable membrane of a silicon pressure sensor element would be too fragile to be in contact with a mechanical transmitting mechanism, such as the mechanism disclosed in U.S. Pat. No. 6,450,038.

It is therefore desirable to develop an improved implantable active silicon pressure sensor that is hermetically sealed to prevent leakage when used in a fluid environment without the drawbacks of the conventional apparatus heretofore used.

SUMMARY OF THE INVENTION

An aspect of the present invention is to develop an autonomous reading implantable active silicon pressure sensor that does not require an external power source to be energized.

Another aspect of the present invention is directed to a hermetically encapsulated relatively long term implantable active pressure sensor that substantially prevents or minimizes leakage even when subject to a fluid environment.

Yet another aspect of the present invention relates to an implantable active pressure sensor suitable for priming so as to minimize or eliminate air inside the fluidic compartment.

Still another aspect of the present invention is directed to an implantable active pressure sensor that eliminates the need for electronic feed throughs at the fluid and electronic interface.

While another aspect of the present invention relates to an implantable active pressure sensor that minimizes sensor temperature dependency and drift.

One more aspect of the present invention is directed to an implantable active pressure sensor in which the sensor electronics are shielded to substantially prevent or minimize against unwanted electromagnetic interference.

Yet another aspect of the present invention is directed to an implantable active pressure sensor in communication with an external device for subsequent transfer of recorded pressure data from the implant to the external device.

An embodiment of the present invention is directed to an implantable active pressure transducer including a pressure sensing element and associated sensor circuitry together are enclosed within an innermost glass packaging. The pressure sensing element is anodically bonded to the innermost packaging substantially aligned with an opening defined therein. An outermost biocompatible metal packaging forms a cavity divided into first and second chambers by an intermediate partition. The innermost packaging is disposed within the first chamber without physically directly contacting or being fixed to the outermost packaging. A barrier plate is hermetically sealed to the intermediate partition to substantially prevent a pressure transmitting fluid from the first chamber flowing into the second chamber where a battery and communication circuitry are disposed. Inductive coupling is used to communicate data detected by the pressure sensing element internally within the implant.

An exemplary embodiment of the present invention is directed to an implantable active pressure transducer including a pressure sensing element and sensor circuitry electrically connected to and operating the pressure sensing element. An innermost packaging encloses the pressure sensing element and the sensor circuitry. The innermost packaging has an opening defined therein. The pressure sensing element is bonded, e.g., anodically bonded, to the innermost packaging substantially aligned with the opening defined therein. An outermost packaging made of a metal, preferably a biocompatible metal, forms an interior cavity divided into first and second chambers. The innermost packaging is disposed within the first chamber without being affixed to the outermost packaging. An inlet and an outlet defined in the outermost packaging both in fluid communication with the first chamber for allowing a flow of a pressure transmitting fluid into the outermost packaging and through the opening defined in the innermost packaging so as to be in contact with the pressure sensing element. A battery disposed within the second chamber is electrically connected to power communication circuitry disposed within the second chamber, the communication circuitry and battery being hermetically isolated from the pressure transmitting fluid in the first chamber.

Another exemplary embodiment of the present invention relates to a method for operating the implantable active pressure transducer as described in the preceding paragraph. Initially, a data signal is transmitted from the first antenna to the second antenna via a first inductive coupling. Thereafter, the data signal is transmitted from a second antenna to the communication circuitry via a first electrical wiring. The data signal from the communication circuitry is retrieved by a third antenna via a second electrical wiring. Wireless transmission between a fourth antenna associated with an external device and the third antenna is established via a second inductive coupling.

Yet another exemplary embodiment of the present invention is directed to a medical device including an innermost packaging enclosing first electronic circuitry associated with the medical device; and an outermost packaging made of a metal forming an interior cavity divided into first and second chambers by a hermetically sealed interface structure free of any electrical connection feed-throughs defined therein; the innermost packaging being disposed within the first chamber. A first inductive coupling is used to establish communication between a first antenna and a second antenna, wherein the first antenna is disposed interior of the innermost packaging and interior of the first chamber; and wherein the second antenna is disposed exterior of the innermost packaging but interior of the first chamber of the outermost packaging. A third antenna is disposed exterior of the outermost packaging. Communication is established between the second and third antennas by way of respective electrical wiring to second electronic circuitry.

Still another exemplary embodiment of the present invention relates to a system including a medical device and an external device. The medical device includes an innermost packaging enclosing first electronic circuitry associated with the medical device; and an outermost packaging made of a metal forming an interior cavity divided into first and second chambers by a hermetically sealed interface structure free of any electrical connection feed-throughs defined therein; the innermost packaging being disposed within the first chamber. A first inductive coupling is used to establish communication between a first antenna and a second antenna, wherein the first antenna is disposed interior of the innermost packaging and interior of the first chamber; and wherein the second antenna is disposed exterior of the innermost packaging but exterior of the first chamber of the outermost packaging. A third antenna is disposed exterior of the outermost packaging. Communication is established between the second and third antennas by way of respective electrical wiring to second electronic circuitry associated with the medical device. The external device includes a fourth antenna in wireless communication with the third antenna of the medical device.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which.

DETAILED DESCRIPTION OF THE INVENTION

Figure 1:
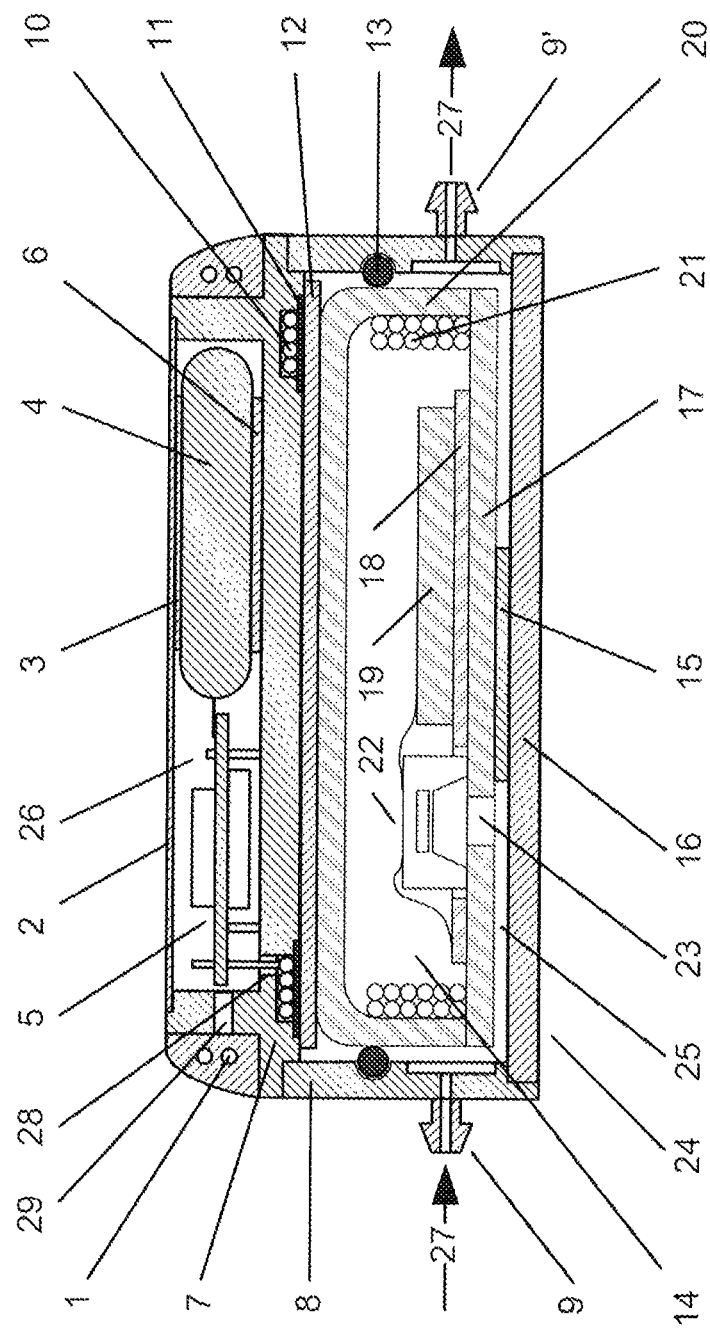
FIG. 1 is a cross-sectional view of an exemplary implantable active pressure transducer in accordance with the present invention.

In resolving the aforementioned problems associated with conventional implantable active pressure transducers, certain design constraints were satisfied. Due to the size of the implantable active pressure transducer, a non-fragile material such as metal (e.g., titanium) rather than glass is used for the outermost packaging or enclosure. Titanium is a desired metal of choice due to its biocompatible properties. The pressure transmitting medium passes freely within the metallic hermetically sealed outermost enclosure or packaging so as to deflect the membrane associated with the pressure sensor.

Semiconductor implantable active pressure transducers are typically made of silicon. Anodic bonding is a well known method for hermetically and permanently bonding silicon to glass without the use of adhesives. Silicon and glass components are heated to a temperature preferably in the range of between approximately 300° C.-approximately 500° C., depending on the glass type. At such temperatures, alkali metal ions in the glass become mobile, A relatively high voltage (e.g., approximately 250 V-approximately 1000 V) is applied across the components as they are brought proximate or in contact with one another causing the alkali cations to migrate from the interface resulting in a depletion layer with relatively high electric field strength. By way of example, an electric field (E) of approximately 500 MV/m (500 V/um) applied to a depletion region approximately 1 um thick produces electrostatic forces that are proportional to $E^2$. This resulting electrostatic attraction brings the silicon and glass components into intimate contact with one another. Further current flow of the oxygen anions from the glass to the silicon results in an anodic reaction and hence a permanent chemical bond at the interface between the two components. Moreover, anodically bondable glass in which the coefficient of thermal expansion (CTE) of the glass substantially matches that of the silicon has been developed, for example, that manufactured by Hoya Corporation USA under the name SD-2 Glass Substrate and Asahi Glass Co., Ltd. as SW-Glass. Using a glass engineered to have a CTE substantially matching that of the silicon is preferred in that it minimizes any dependency between sensor temperature and pressure measurement drift. That is, regardless of variation in sensor temperature, the substantially matched CTE between the two components will minimize any mechanical stress within the silicon pressure sensor.

The pressure sensor is made of silicon and the outermost enclosure or packaging is made of titanium. Heretofore, no recognized methods exist for bonding or assembling titanium to either silicon or glass that exhibit the following properties: (i) relatively long term mechanical stability; and (ii) matching of a coefficient of thermal expansion (CTE) between the two materials. Since the pressure transducer is to be implanted in the body, poor long term mechanical stability would negatively impact on its overall operation and require explanation, not to mention possible detriment to the health of the patient. Unmatched CTE between silicon and titanium causes mechanical stress at the interface resulting from variations in temperature that produces unwanted pressure measurement drift.

As a result, it is undesirable for the pressure sensing element to be bonded directly to a titanium enclosure. To satisfy this design criteria, the present inventive pressure sensor transducer employs at least two enclosures or packaging that are not fixed, soldered or bonded to one another. A first or innermost enclosure or packaging 14 made of glass in which a silicon pressure sensing element 22 is enclosed, for example, as disclosed in U.S. Pat. No. 4,875,134 herein incorporated by reference in its entirety. Pressure sensing element 22 may be either a capacitive pressure sensing element or a piezoelectric pressure sensing element. Preferably, the exterior surface of the glass enclosure 14 is coated with a biocompatible polymer such as a parylene biocompatible film. The first or innermost enclosure or packaging 14 includes a cover 20 and a base plate 17 having a hole 23 defined therein. Silicon pressure sensing element 22 is anodically bonded to the glass base plate 17 so that it is substantially aligned with the hole or opening 23 defined therein. In order to minimize any mechanical stress at the interface between the silicon pressure sensing element 22 and the glass base plate 17 resulting from variations in temperature, the glass used for the base plate 17 preferably has a CTE substantially matching that of the silicon pressure sensing element 22. It should be noted that since the pressure sensing element 22 is not bonded to the cover 20, unlike the glass material preferably used for the base plate 17, the glass material used for cover 20 need not have a CTE substantially matching that of the silicon pressure sensing element 22. Sensor electronics 19 mounted on a printed circuit board 18 and wired to pressure sensing element 22 are also encapsulated within the glass packaging 14.

Figure 2:
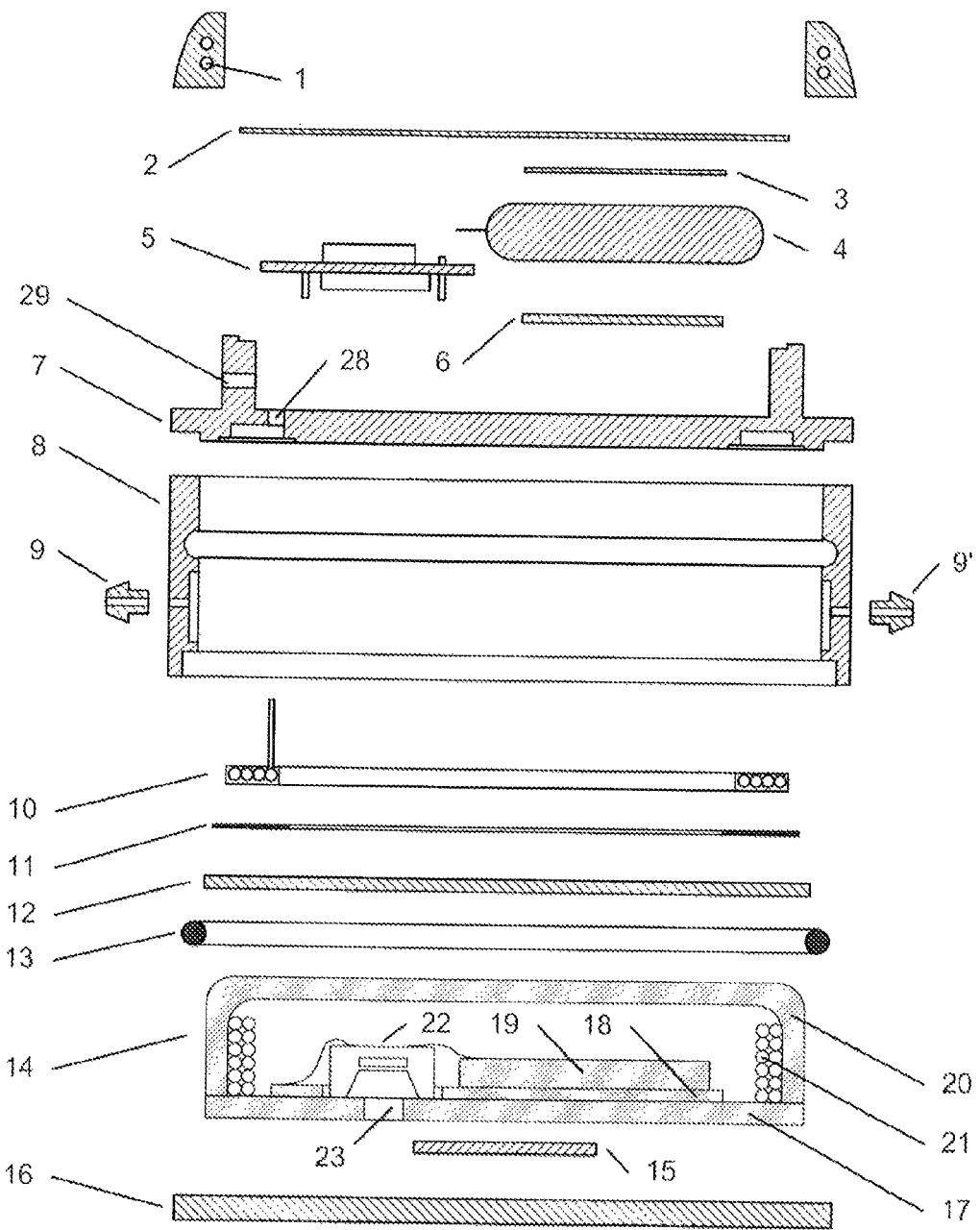
FIG. 2 is an exploded view of the implantable active pressure transducer of FIG. 1.

The first or innermost glass enclosure or packaging 14 is, in turn, enclosed in without being soldered, bonded or fixed to a second or outermost metal enclosure or packaging 24, preferably made of titanium or other biocompatible metal material. Unlike glass, the titanium packaging 24 is able to accommodate the size requirements for an implantable active pressure transducer without being fragile. This second or outermost enclosure or packaging 24 is formed by cover 2, cylinder 8 (forming the side walls of the enclosure 24) and base plate 16. The outermost enclosure or packaging 24 is subdivided by a hermetically sealed interface structure into two chambers 25, 26. FIGS. 1 & 2 depict the hermetically sealed interface structure comprising two elements, e.g., an intermediate partition 7 and barrier plate 11, assembled together, preferably welded. As an alternative to that show in the figures, the hermetically sealed interface structure may be designed as a single machined component rather than multiple components assembled together. A first chamber 25 of the outermost enclosure 24 includes a titanium inlet 9 and outlet 9' formed in its cylindrical walls 8 that allow the passage of a pressure transmitting medium or fluid (e.g., oil or mercury) freely therethrough. The inlet and outlet 9, 9', respectively, may alternatively be on the same side of the outermost titanium enclosure 24. Flow of a pressure transmitting fluid or medium 27 injected via the inlet 9 of the into the first chamber 25 of the outermost titanium enclosure 24 may be directed by a fluidic path defined by spacer 15 to the opening 23 defined in the base plate 17 and in contact with the pressure sensing element 22. It is contemplated and within the intended scope of the present invention for spacer 15 to be eliminated so long as the pressure transmitting medium remains free to flow in the first chamber 25 and enter the opening 23 defined in the base plate 17 so as to be in contact with the pressure sensing element 22. Additional spacers 3, 6 within the second chamber 26 provide mechanical support for battery 4. This second chamber 26 of the titanium enclosure 24 shields or minimizes exposure by the electronics to deleterious electromagnetic interference so as to comply with medical industry standards while maintaining a hermetically sealed enclosure.

Since glass and titanium have different CTEs if the two enclosures 14, 24 were fixed to or in direct contact with one another any variation in temperature would cause mechanical stress on pressure sensing element 22 resulting in undesirable pressure measurement drift over time. In order to minimize long term drift in pressure readings, the innermost glass enclosure 14 is designed so as not to be fixed to or directly contact the outermost titanium enclosure 24. In short, the innermost glass enclosure 14 floats freely within the first chamber 25 without direct physical contact or being fixed to the outermost titanium enclosure 24. To achieve this goal, the innermost glass enclosure 14 may be wedged or retained in position from all sides without being physically fixed or connected to the outermost titanium enclosure 24. In particular, a pair of spacers 12, 15 may be disposed above and below the innermost glass enclosure 14. Spacers 12, 15 are preferably disc shape. An O-ring 13 prevents contact between the sides of the innermost glass enclosure 14 and outermost titanium enclosure 24 while X-Y locating the innermost enclosure relative to the outermost enclosure. Spacers 12, 15 and O-ring 13 are preferably made of a polymer, e.g., silicone. In addition, the spacers 12, 15 and O-ring 13 serve a dual purpose of providing mechanical support while simultaneously acting as a cushion of mechanical stresses between the glass and titanium interfaces due to variation in temperature so as to minimize any long term drift in pressure measurement readings over time. Fluid is prevented by intermediate partition 7 from entering the second chamber 26 of the outermost enclosure 24 that houses a battery 4 used to power the implantable pressure transducer and associated electronic circuitry 5.

Another significant design criteria met by the present inventive implantable active pressure transducer is to maintain a long term hermetic sealed interface or barrier between the fluids and the electronics of the pressure sensor or transducer. Any feed-throughs as a result of wires at the fluid and electronics interface are subject to possible leakage and thus have been eliminated. As discussed above, a pressure transmitting medium is permitted to flow freely via the inlet 9 and outlet 9' inside the first chamber 25 of the outermost titanium enclosure 24. To eliminate wired electrical connection feed-throughs at the interface between fluid and electronics, the present invention employs two inductive couplings achieved using three antenna associated with the implantable active pressure transducer and one antenna associated with an external device. A first inductive coupling is established within the implantable active pressure transducer. This first inductive coupling is established between a first antenna 21 (disposed within the first chamber 25 of the outermost titanium enclosure 24 but interior of the innermost glass enclosure 14) and a second antenna 10 (located exterior of the innermost glass enclosure 14 and exterior of the first chamber of the outermost titanium enclosure 24).

Intermediate partition 7 is made of a material, preferably a metal, of sufficient thickness to substantially reduce or prevent electromagnetic field exposure by the sensor electronics 19. As a result, it is difficult to establish an inductive coupling across intermediate partition 7 between the first and second chambers 25, 26, respectively. Communication of information from within to outside of the first chamber 25 of the outermost enclosure 24 may therefore be realized by electrically connecting each of antennas 1 and 10 to communication circuitry 5 by way of a first electric feed-through hole 28 in intermediate partition 7. Hole 28 is fluidically isolated from wet chamber 25 via barrier plate 11 that is preferably laser welded to partition 7. A second electric feed-through hole 29 is defined in intermediate partition 7 to pass the wire through that connects antenna 1 to electronics 5. The first antenna 21 is preferably a helical coil encircling the pressure sensing element 22 disposed within and proximate the innermost glass enclosure 14. Located exterior of the innermost glass enclosure 14 and exterior of the first chamber 25 of the outermost titanium enclosure 24, is the second antenna 10. As shown in the figures, the second antenna 10 is a coil disposed between intermediate partition 7 and a barrier plate 11. Barrier plate 11 therefore serves a dual function of forming a hermetic seal with intermediate partition 7 to prevent flow of pressure transmission fluid from the first chamber 25 into the second chamber 26 while simultaneously supporting the second antenna 10 against intermediate partition 7. By way of illustrative example, both intermediate partition 7 and barrier plate 11 are made of titanium and preferably laser welded to form a hermetic seal therebetween.

Figure 3:
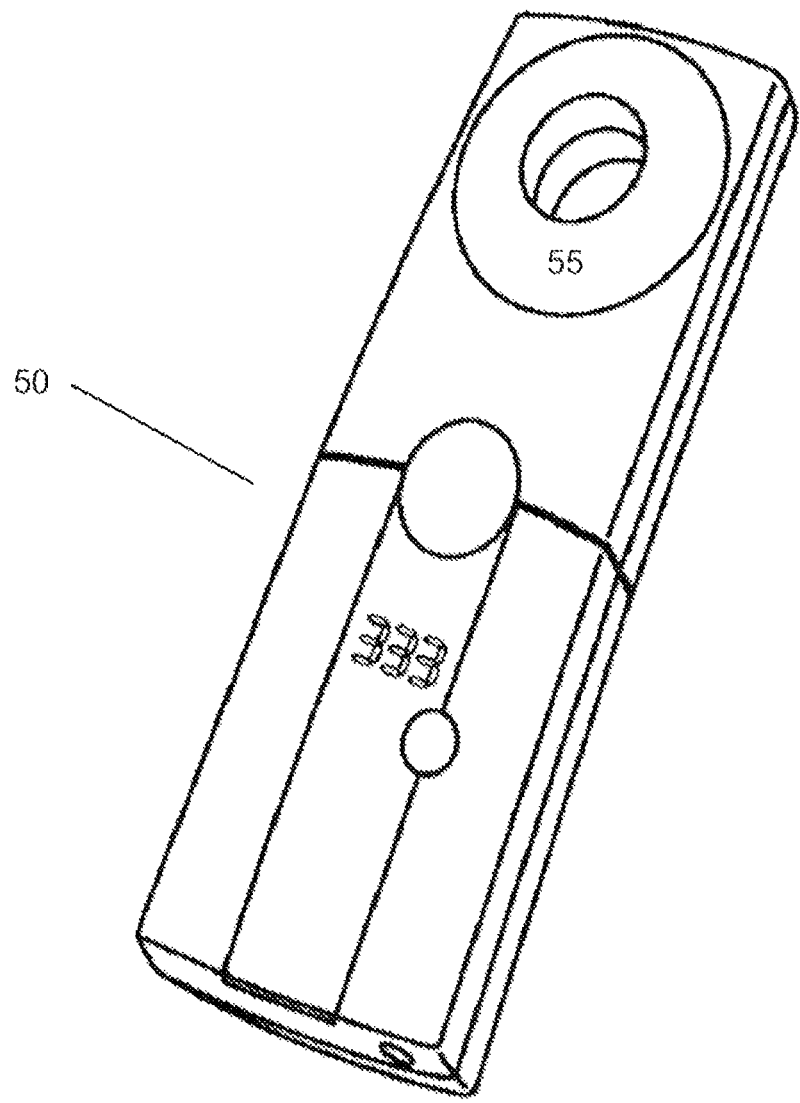
FIG. 3 is a perspective view of an exemplary external control device for controlling the implantable active pressure transducer wirelessly.

Communication between the implantable active pressure transducer and an external device 50 (e.g., programmer or reader) is preferably wireless. Such wireless communication may be realized by establishing a second inductive coupling between a third antenna 1 disposed outside of the outermost packaging 24 of the implantable active pressure transducer and a fourth antenna 55 associated with an external device 50 (as shown in FIG. 3). In a preferred embodiment, the third antenna 1 is a wire made of a biocompatible metal, e.g., titanium, or a non-biocompatible metal that is over molded in a biocompatible polymer.

The four antennas 1, 10, 21 and 55 may be loop antennas whereby both first and second inductive couplings are used to transmit both energy and data. Alternatively, since the third antenna 1 is connected to communication circuitry 5 powered by battery 4, and the fourth antenna 55 associated with external device 50 is also connected to electronics having its own power supply associated with the external control device 50, the second inductive coupling between the fourth antenna 55 and the third antenna 1 may be replaced by a standard radio-frequency link. In this case, each of the third and fourth antenna 1, 55, respectively, are other than loop antenna and connected to an active (battery powered) transceiver (transmitter receiver) thus no energy need be transmitted. However, note that in this latter embodiment, the lifetime of the implant is dependent on the amount of implant communications which drains energy from the implantable battery 4.

Pressure measurement readings generated by the sensor electronics 19 (e.g., signal conditioning circuitry as well as passive telemetry RF for communication with second antenna 10 connected to electronics 5) are transmitted internally by way of the first inductive coupling between the first antenna 21 and the second antenna 10. In turn, the signal is transmitted between the second antenna 10 and the third antenna 1 via communication circuitry 5 to which each of antennas 1 and 10 are electrically connected via a wire. Since the third antenna 1 is disposed outside of the titanium packaging or enclosure 14 the signal received by it may be transmitted via the second inductive coupling to the external device 50 such as a control unit or reader. Of course, control or programming signals generated by the external device 50 may, in turn, be transmitted back to the implantable active pressure transducer.

The innovative design of the present inventive hermetically sealed active implantable silicon pressure transducer makes it particularly well suited for relatively long-term implantation, for example, ranging from approximately 5 years to approximately 10 years. In addition, the internal inductive coupling between antennas 10 and 21 associated with the implantable pressure transducer eliminates feed-through wires that pose a risk of leakage at the fluid-electronic interface. The substantial matching of the coefficient of thermal expansion of glass base plate of the innermost glass packaging to that of the silicon pressure sensing element substantially decouples the pressure measurement readings from variations in the temperature of the sensor. Similarly, the floating of the innermost glass packaging so as to preclude any fixation or direct physical contact with the outermost titanium packaging minimizes any drift in pressure measurement readings due to variations in temperature of the sensor. Lastly, the priming or filing of the first chamber 25 with pressure transmitting medium displaces any air therein and thus minimizes or substantially prevents any damping of the pressure signal measured by the sensor.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. An implantable active pressure transducer comprising:
   a pressure sensing element;
   sensor circuitry for operating the pressure sensing element, the sensor circuitry electrically connected to the pressure sensing element;
   an innermost packaging enclosing the pressure sensing element and the sensor circuitry; the innermost packaging having an opening defined therein; the pressure sensing element being bonded to the innermost packaging substantially aligned with the opening defined therein;
   an outermost packaging made of a metal forming an interior cavity divided into first and second chambers; the innermost packaging being disposed within the first chamber without being fixed to the outermost packaging; the outermost packaging having an inlet and an outlet both in fluid communication with the first chamber for allowing a flow of a pressure transmitting fluid into the outermost packaging and through the opening defined in the innermost packaging so as to be in contact with the pressure sensing element;
   communication circuitry disposed within the second chamber; and
   a battery disposed within the second chamber and electrically connected to power the communication circuitry, the communication circuitry and battery being hermetically isolated from the pressure transmitting fluid in the first chamber.

2. The transducer according to claim 1, wherein the pressure sensing element is made of silicon; the innermost packaging is made of glass; and the metal forming the outermost packaging is titanium.

3. The transducer according to claim 2, wherein the glass selected for at least a portion of the innermost packaging at an interface in which the pressure sensing element is anodically bonded to it has a coefficient of thermal expansion substantially matching that of the pressure sensing element.

4. The transducer according to claim 1, further comprising at least one spacer disposed between the inmost and outermost packaging to: (i) provide mechanical support to prevent any direct physical contact between the innermost and outermost packaging; (ii) direct the flow of the pressure transmitting fluid through the opening defined in the innermost packaging; and (iii) act as a cushion for mechanical stresses at interfaces between the innermost and outermost packaging due to variation in temperature so as to minimize any long term drift in pressure measurement readings over time.

5. The transducer according to claim 1, further comprising a hermetically sealed interface structure dividing the interior cavity of the outermost packaging into the first and second chambers to substantially prevent passage of the pressure transmitting fluid between the chambers.

6. The transducer according to claim 5, wherein the hermetically sealed interface structure is formed from a single integrated component.

7. The transducer according to claim 5, wherein the hermetically sealed interface partition comprises:
an intermediate partition; and
a barrier plate hermetically sealed to the intermediate partition to form a primary barrier substantially preventing the pressure transmitting fluid from the first chamber flowing into the second chamber.

8. The transducer according to claim 5, further comprising:
a first disc spacer disposed between the respective innermost and outermost packaging, the first disc spacer defining a fluidic path directing the pressure transmitting fluid through the opening defined in the innermost packaging and in contact with the pressure sensing element;
a second disc spacer disposed between the innermost packaging and the hermetically sealed interface structure; and
an O-ring disposed between the innermost and outermost packaging.

9. The transducer according to claim 8, wherein the first disc spacer, the second disc spacer and the O-ring are all made of silicone.

10. The transducer according to claim 1, further comprising:
a first inductive coupling for establishing communication between a first antenna disposed within the innermost packaging and a second antenna disposed exterior of the innermost packaging but within the first chamber of the outermost packaging.

11. The transducer according to claim 10, wherein the first antenna is a helical coil encircling the pressure sensing element and the sensor electronics.

12. The transducer according to claim 10, further comprising a hermetically sealed interface structure dividing the interior cavity of the outermost packaging into the first and second chambers to substantially prevent passage of the pressure transmitting fluid between the chambers, wherein the second antenna is disposed in the second chamber.

13. The transducer according to claim 10, further comprising a third antenna disposed exterior of the outermost packaging.

14. The transducer according to claim 13, wherein the third antenna 1 is a metallic wire that is made of a biocompatible material or a non-biocompatible material over molded in a biocompatible polymer.

15. The transducer according to claim 13, further comprising:
an intermediate partition dividing the interior cavity into the first and second chambers; and
a barrier plate hermetically sealed to the intermediate partition to form a primary barrier substantially preventing the pressure transmitting fluid from the first chamber flowing into the second chamber;
wherein the intermediate partition has defined therein a first feed-through hole through which a first wired electrical connection is established between the second antenna and the communication circuitry; the intermediate partition having defined therein a second feed-through hole through which a second wired electrical connection is established between the third antenna and the communication circuitry.

16. A method for operating the implantable active pressure transducer in accordance with claim 13, comprising the steps of:
transmitting a data signal from the first antenna to the second antenna via the first inductive coupling; and
transmitting the data signal from the second antenna to the communication circuitry via first electrical wiring.

17. The method according to claim 6, further comprising the step of retrieving the data signal by the third antenna from the communication circuitry via second electrical wiring.

18. The method according to claim 17, further comprising the step of wirelessly transmitting the retrieved data signal from the third antenna to a fourth antenna associated with an external device via a second inductive coupling.

19. The method according to claim 16, wherein the pressure sensing element is made of silicon; the innermost packaging is made of glass; and the metal forming the outermost packaging is titanium.

20. The method according to claim 19, wherein the glass selected for at least a portion of the innermost packaging at an interface in which the pressure sensing element is anodically bonded to it has a coefficient of thermal expansion substantially matching that of the pressure sensing element.

21. The method according to claim 16, further comprising at least one spacer disposed between the inmost and outermost packaging: (i) provide mechanical support to prevent any direct physical contact between the innermost and outermost packaging; (ii) direct the flow of the pressure transmitting fluid through the opening defined in the innermost packaging; and (iii) act as a cushion for mechanical stresses at interfaces between the innermost and outermost packaging due to variation in temperature so as to minimize any long term drift in pressure measurement readings over time.

22. The method according to claim 21, wherein the first disc spacer, the second disc spacer and the O-ring are all made of silicone.

23. The method according to claim 22, further comprising a hermetically sealed interface structure dividing the interior cavity of the outermost packaging into the first and second chambers to substantially prevent passage of the pressure transmitting fluid between the chambers, wherein the first antenna is a helical coil encircling the pressure sensing element and the sensor electronics; and the second antenna is disposed within the second chamber.

24. The method according to claim 23, wherein the third antenna 1 is a metallic wire that is made of a biocompatible material or a non-biocompatible material over molded in a biocompatible polymer.

25. A medical device comprising:
an innermost packaging enclosing first electronic circuitry associated with the medical device;
an outermost packaging made of a metal forming an interior cavity divided into first and second chambers by a hermetically sealed interface structure free of any electrical connection feed-throughs defined therein; the innermost packaging being disposed within the first chamber;

a first inductive coupling for establishing communication between a first antenna and a second antenna, wherein the first antenna is disposed interior of the innermost packaging and interior of the first chamber; and wherein the second antenna is disposed exterior of the innermost packaging and exterior of the first chamber of the outermost packaging; and a third antenna disposed exterior of the outermost packaging, communication being established between the second and third antennas by way of respective electrical wiring to second electronic circuitry.

26. A system comprising:

a medical device including:
   an innermost packaging enclosing first electronic circuitry associated with the medical device;
   an outermost packaging made of a metal forming an interior cavity divided into first and second chambers by a hermetically sealed interface structure free of any electrical connection feed-throughs defined therein; the innermost packaging being disposed within the first chamber;

a first inductive coupling for establishing communication between a first antenna and a second antenna, wherein the first antenna is disposed interior of the innermost packaging and interior of the first chamber; and wherein the second antenna is disposed exterior of the innermost packaging and exterior of the first chamber of the outermost packaging; and a third antenna disposed exterior of the outermost packaging, communication being established between the second and third antennas by way of respective electrical wiring to second electronic circuitry associated with the medical device; and an external device including a fourth antenna in wireless communication with the third antenna of the medical device.

\* \* \* \* \*